United States Patent
Romero et al.

(10) Patent No.: US 10,203,276 B2
(45) Date of Patent: Feb. 12, 2019

(54) METHOD FOR INSPECTING A CASING BY COLORIMETRY

(71) Applicant: Safran Aircraft Engines, Paris (FR)

(72) Inventors: Jean-Louis Romero, Moissy-Cramayel (FR); Jean-Pierre Coulette, Moissy-Cramayel (FR); Angélique Melody Marine Alexia Mainczyk, Moissy-Cramayel (FR)

(73) Assignee: Safran Aircraft Engines, Paris (FR)

( * ) Notice: Subject to any disclaimer, the term of this patent is extended or adjusted under 35 U.S.C. 154(b) by 0 days.

(21) Appl. No.: 15/901,509

(22) Filed: Feb. 21, 2018

(65) Prior Publication Data

US 2018/0306707 A1    Oct. 25, 2018

Related U.S. Application Data

(60) Provisional application No. 62/462,154, filed on Feb. 22, 2017.

(30) Foreign Application Priority Data

Mar. 8, 2017    (FR) ...................................... 17 51897

(51) Int. Cl.
*G01N 21/25* (2006.01)
*G01N 33/44* (2006.01)

(52) U.S. Cl.
CPC ......... *G01N 21/251* (2013.01); *G01N 21/255* (2013.01); *G01N 33/44* (2013.01)

(58) Field of Classification Search
CPC .... G01N 21/25; G01N 21/251; G01N 21/255; G01N 33/44; A61K 8/19; A61K 8/26;
(Continued)

(56) References Cited

U.S. PATENT DOCUMENTS

| | | | |
|---|---|---|---|
| 2005/0067569 A1 | 3/2005 | Shelley et al. | |
| 2012/0242009 A1* | 9/2012 | Mullane | ................ A61F 13/513 264/405 |
| 2014/0096350 A1 | 4/2014 | Denton et al. | |

FOREIGN PATENT DOCUMENTS

| | | |
|---|---|---|
| JP | 61-59242 A | 3/1986 |
| JP | 2008-180607 A | 8/2008 |
| WO | WO 2013/050691 A1 | 4/2013 |

* cited by examiner

*Primary Examiner* — Abdullahi Nur
(74) *Attorney, Agent, or Firm* — Blank Rome LLP (57) ABSTRACT

A method for non-destructively testing the heating of a determined zone of a part made of a polymer material, comprising: a) taking at least one colorimetric measurement on said determined zone to be tested and obtaining the values $a_p$, $b_p$ and $L_p$ of the parameters a, b and L of the CIELAB colorimetric space; b) taking at least one colorimetric measurement on said reference zone of the part and obtaining the values $a_{p/ref}$, $b_{p/ref}$ and $L_{p/ref}$ of the parameters a, b and L of the CIELAB colorimetric space; c) calculating the colour difference $\Delta E_p$ between the colorimetric measurements obtained in steps a) and b); and d) from the value $\Delta E_p$, determining the time period during which said zone to be tested of the part has been subjected to a determined heating temperature, by using a reference database.

7 Claims, 6 Drawing Sheets

(58) Field of Classification Search
CPC ... A61K 8/73; A61K 8/49; A61K 8/81; A61K 8/58
See application file for complete search history.

METHOD FOR INSPECTING A CASING BY COLORIMETRY

CROSS-REFERENCE TO RELATED APPLICATIONS

This application claims the benefit of U.S. Provisional Patent Application No. 62/462,154, filed Feb. 22, 2017, and French Patent Application No. 1751897, filed Mar. 8, 2017, the contents of each of which are incorporated herein by reference.

TECHNICAL FIELD

The present invention relates to a method for non-destructively testing a part comprising a matrix, for example, made of polymer. In particular, reinforcing fibres can be integrated to the matrix.

BACKGROUND

Conventionally, the upstream end of a turbine engine comprises a fan comprising a wheel formed of a plurality of blades surrounded on the outside by an annular casing which can made of a metal material or of a composite material comprising a matrix integrating reinforcing fibres, such as a polymer matrix, for example, epoxide polymer, and carbon fibre or glass fibre reinforcing fibres. This casing enables an initial compression of air entering in the turbine engine and also ensures a function for confining the blades in case of loss of one of them. The fan casing is surrounded by a plurality of equipment supply ducts, in particular, by a pressurised air supply duct, at a temperature of around 200° C., an engine called APU (auxiliary power unit) used to start the turbojet as well as supplying the aircraft cabin with electricity when the aircraft is grounded.

In case of malfunctioning, such as a leak from the pressurised air supply duct, the air can lead to a significant local heating of the casing, since the temperature of the air is around 200° C. When the casing is made of a metal material, for example, aluminium, the heating is not impacted by the mechanical integrity of the casing. In the case of a matrix fan case integrating the reinforcing fibres, the mechanical strength thereof following being heated, must be able to be guaranteed.

Therefore, it is understood that the non-destructive test of a composite matrix casing with reinforcing fibres is particularly important, and all the more so, as a composite casing is proving to be very expensive.

It has thus been proposed to apply thermosensitive paints on the casing. However, the lifespan of these paints highly limits their interest, since an engine can be used for period longer than the lifespan of these paints, in particular for long- or medium-haul aircraft. Furthermore, during the placing of an engine, this conventionally undergoes cleaning by scraping, which causes a total removal of the layer of thermosensitive paint, involving another step of applying a layer of paint. Finally, if a thermosensitive paint enables to visually consider the heating state of a given zone of a fan case, it only proves to be an indirect measurement of the state of the internal structure of the casing and does not enable a specific quantification of the internal structure of the casing.

SUMMARY

The invention, in particular, aims to provide a simple, effective and economic solution to the problems of the prior art defined above.

To this end, it proposes a method for non-destructively testing the heating of a zone determined to be tested of a part made of a polymer material, the method comprising the following steps:

a) taking at least one colorimetric measurement on said determined zone to be tested and obtaining the values $a_p$, $b_p$ and $L_p$ of the parameters a, b and L of the CIELAB colorimetric space, b) taking at least one colorimetric measurement on said reference zone of the part and obtaining the values $a_{p/ref}$, $b_{p/ref}$ and $L_{p/ref}$ of the parameters a, b and L of the CIELAB colorimetric space, c) calculating the colour difference $\Delta E_p$ between the colorimetric measurements obtained in steps a) and b), d) from the value $\Delta E_p$ obtained in step c), determining the time period during which said zone to be tested of the part has been subjected to a determined heating temperature and determining said heating temperature, by using a reference database comprising the values $\Delta E'$ of colour differences obtained from a plurality of samples made of a polymer material that has been subjected to a determined temperature for a determined time period.

The difference $\Delta E$ between two colours corresponds to the distance, more specifically the Euclidian distance, between the two colours placed in the CIELAB colour space meaning the CIE L*a*b* system, or the acronym CIE means the Commission Internationale de l'Eclairage (International Lighting Commission). The asterixis have voluntarily been omitted in the text to avoid encumbering the notations.

In the present document, the CIELAB space corresponds to that defined by the standard NF EN ISO 11664-4 (2011-07-01), of which the title is "Colorimétrie—Partie 4: espace chromatique L*a*b* CIE 1976" ("Colorimetry—Part 4: CIE L*a*b* colour space 1976").

The value $\Delta E_p$ is determined for said zone to be tested by making the calculation $\Delta E_p = \sqrt{L_p^2 + \Delta a_p^2 + \Delta b_p^2}$.

The values $\Delta E'$ are determined similarly for each first sample from the database.

The invention proposes to take a direct measurement of the state of the polymer structure of the casing by colorimetry, and to compare the colour difference $\Delta E_p$ obtained on the part with colour differences previously obtained on the samples and contents in the database.

According to another characteristic of the invention, the method comprises the following steps:

tracing a graph of the development of $\Delta E'$ over time for several determined temperatures, and carrying out step d) by looking for the intersection of the constant ordinate line $\Delta E_p$ with one of the aforementioned curves.

Again, according to another characteristic of the invention, establishing the reference database comprises, for each first sample, the following steps:

obtaining the values L', a', b', of the respective parameters L, a, b, of the CIELAB colorimetric space, from at least one colorimetric measurement of said first sample, calculating $\Delta a' = a' - a'_{ref}$, calculating $\Delta b' = b' - b'_{ref}$ and calculating $\Delta L' = L' - a'_{ref}$, where:

$a'_{ref}$, $b'_{ref}$ and $L'_{ref}$ correspond respectively to the values of the parameters a, b, L of the CIELAB colorimetric space, these values having been obtained on a second sample made of a polymer material, in particular, of reinforcing fibres, having the same time of existence as said first sample considered and having been kept at a temperature within a range of temperatures, such as that of preserving the mechanical integrity of the second sample, or such as a range between 0 and 40° C., which could further consider the exposure to rays in the ultraviolet field, calculating the colour difference ΔE' between the first sample and the second associated sample.

The values ΔE' are determined for each sample by making the calculation $\Delta E' = \sqrt{\Delta L'^2 + \Delta a'^2 + \Delta b'^2}$.

To limit errors in measurement and to average out the experimental variability, each value considered of the parameters L, a, b of the CIELAB colorimetric space can be obtained by taking the average of at least five successive colorimetric measurements at the place considered.

According to the invention, in case a heating risk is established, the method can also further comprise a subsequent step to step d), of carrying out a physicochemical analysis of the determined zone to be tested of the part, so as to determine on the state of damage of said determined zone.

The part analysed can be made of a polymer material comprising reinforcing fibres.

Preferably, a step of cleaning the surface whereon a colorimetric measurement is intended to be taken, is carried out prior to said colorimetric measurement.

BRIEF DESCRIPTION OF THE DRAWINGS

The invention will be best understood, and other details, advantages and characteristics of the invention will appear upon reading the following description, made as a non-exhaustive example, in reference to the following figures.

DETAILED DESCRIPTION

As explained above, the fan casing 10 represented in FIG. 1, made of polymer, in particular of reinforcing fibres, can undergo when switched on, a local heating that should be able to be characterised by a non-destructive method enabling to determine the state of the casing 10 in order to determine if it can (or not) be kept in service in a turbine engine.

Figure 2:
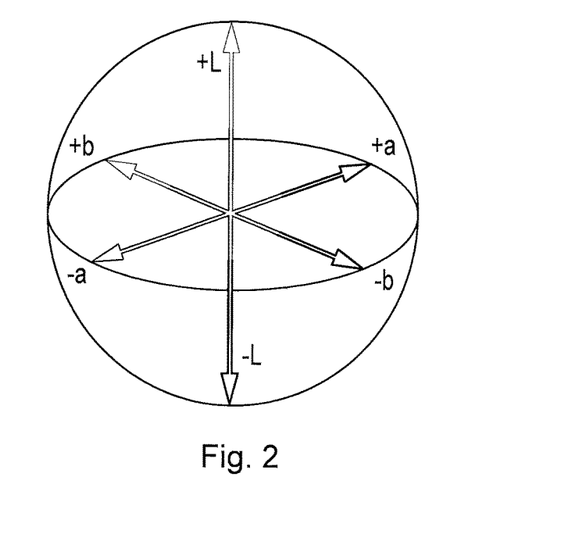
FIG. 2 is a representative view of the CIELAB colorimetric space axes used in the present document.

FIG. 2 represents the CIELAB space used in the present document for analysing colorimetric data obtained on the part to be tested, as well as for establishing the reference database on a plurality of first samples. The CIELAB space is a system which enables to represent the trichromatic components along three orthogonal axes between them. The axis L (or L*) represents the luminance or clarity axis (perfect black: L=0; perfect white: L=100). The axis a (or a*) represents the axis going from green (negative values of a) to red (positive values of a). The axis b (or b*) represents the axis going from blue (negative values of b) to yellow (positive values of b).

It is again reminded, that the space used is the CIE L*a*b*colorimetric space, and that the asterixis have voluntarily been removed as this is usual. In this colour system, a colour difference between a first colour of coordinates $L_1$, $a_1$, $b_1$ and a second colour of coordinates $L_2$, $a_2$, $b_2$ is calculated as follows:

$$\Delta E = \sqrt{\Delta L^2 + \Delta a^2 + \Delta b^2}, \text{ where}$$
$$\Delta L = (L_1 - L_2)$$
$$\Delta a = (a_1 - a_2)$$
$$\Delta b = (b_1 - b_2)$$

This method of calculating the colour difference is the one used later, as this will appear following the description.

The invention proposes to establish a reference database comprising colorimetric measurements according to the CIELAB colour system. The term "reference" used below is to be understood as meaning an element of the reference database comprising colorimetric measurements and more generally, data obtained from the reference samples.

Figure 3:
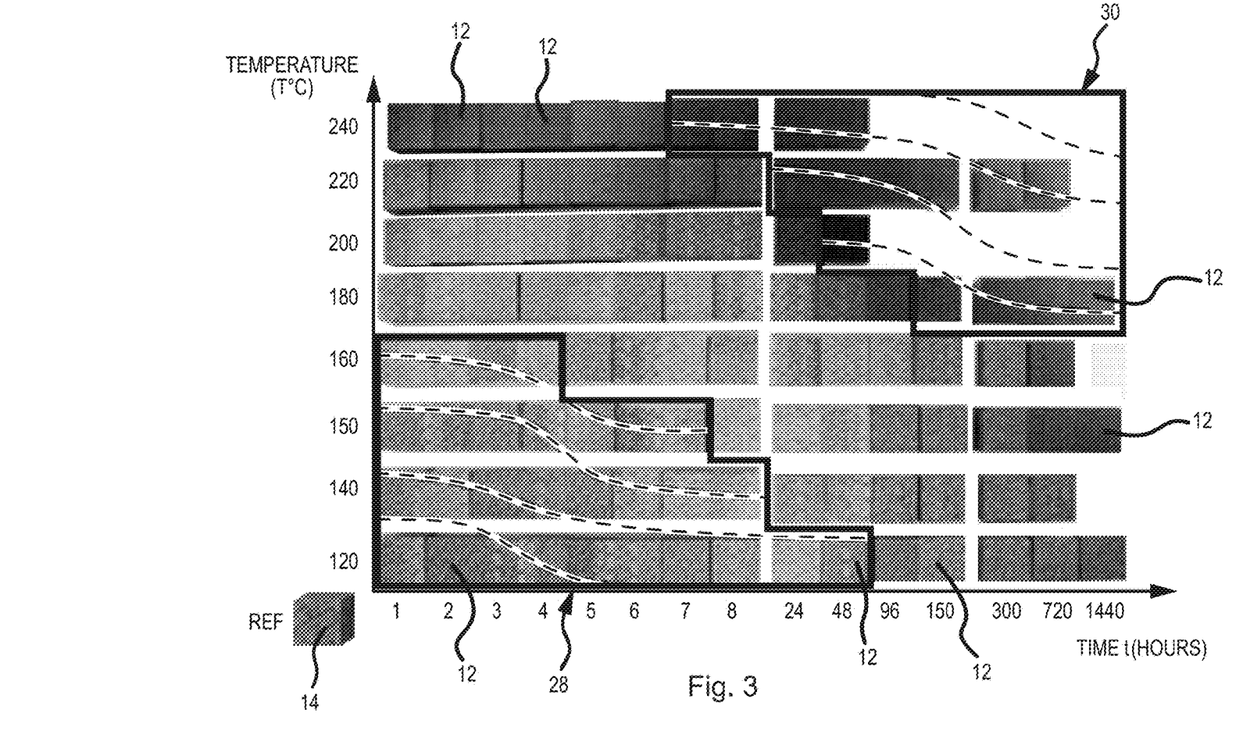
FIG. 3 is a schematic view of a plurality of samples, each having undergone oxidation for a given time (vertically) at a given temperature (horizontally)

For this, a batch of a plurality of first samples 12 of a material similar to the part to be analysed is constituted. FIG. 3 illustrates such a batch which thus comprises several first samples 12 of fan case 10 made of a polymer material, preferably of reinforcing fibres, arranged in the form of lines and columns. Along a given line, each first sample 12 is subjected to a given temperature, of which the exposure time is given by the position along a line. Of course, the database should comprise a number of first samples 12 enabling to realise different levels of thermal oxidation, that the polymer can be subjected to under actual functioning conditions. Thus, the database should comprise the first samples 12 having been subjected to the aforementioned temperatures for periods of time going up to at least 6 months.

Figure 1:
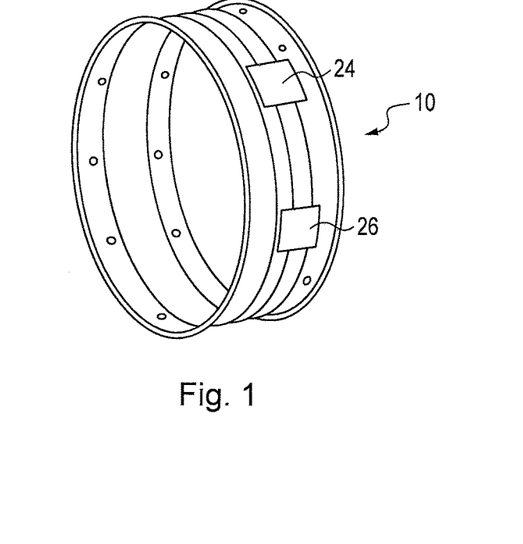
FIG. 1 is a schematic view of a turbine engine fan case to be tested.

In the configuration represented as an example, the first samples 12 have been subjected to temperatures in ° C. of 120, 140, 150, 160, 180, 200, 220 and 240° C. for periods in hours, spread out from 1 up to 1440 hours, which corresponds to a period of 2 months. The sample 14 positioned in the lower left-hand corner in FIG. 1 represents a sample 12 not having been subjected to any heating, which therefore constitutes the absolute reference of a fan case 10 without any thermal heating. It is observed in FIG. 1, that the first samples 12 darken as soon as the temperature increases, and that the exposure time to a temperature increases, which is consistent with a thermal oxidation of the polymer.

Figure 4:
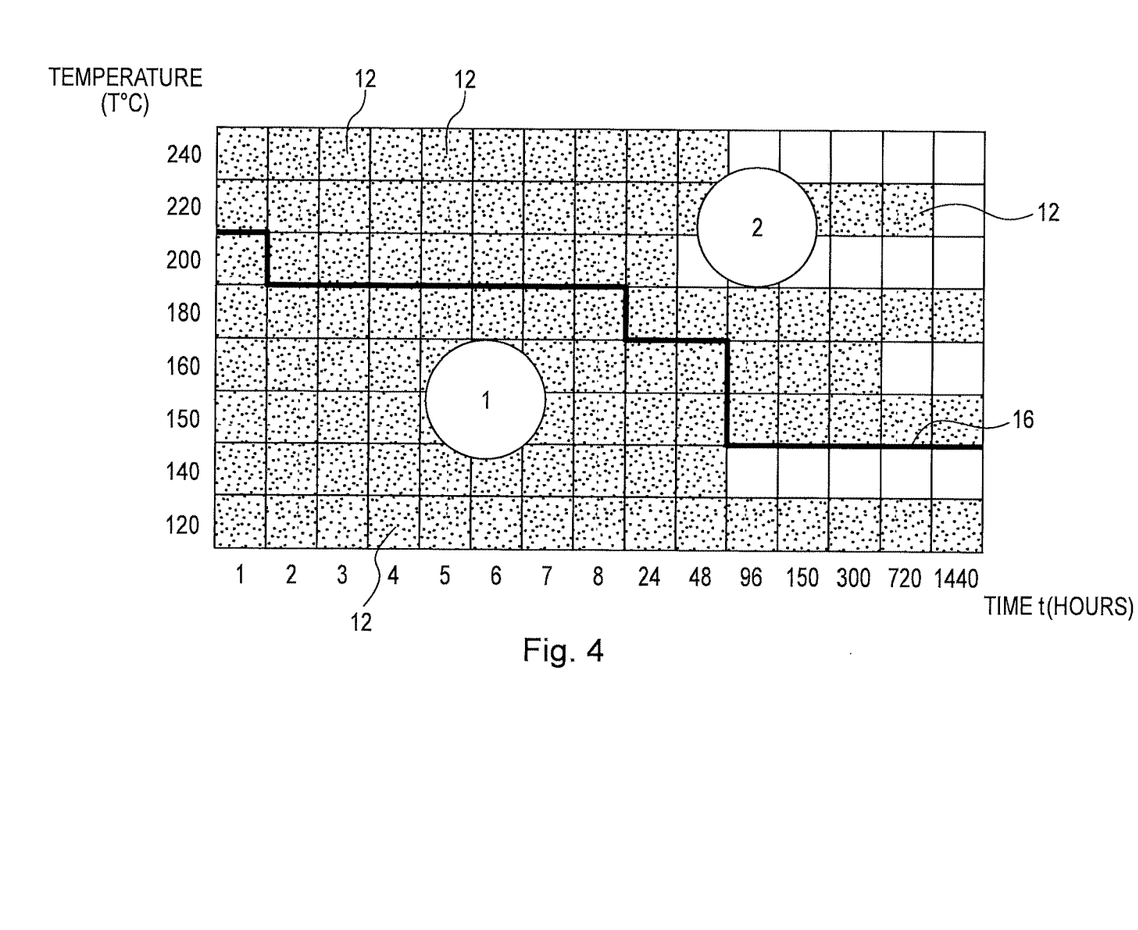
FIG. 4 is a schematic view illustrating a line of separation between a first zone 1 and a second zone 2.

FIG. 4 schematically represents FIG. 3 and comprises a line of separation 16 of a first zone 1 and a second zone 2. The first zone 1 corresponds to the first samples 12 which have been subjected to an acceptable temperature for an acceptable time period, whereas the second zone 2 corresponds to the first samples 12 which have been subjected to too-high temperature for a given time period. Thus, if visually, it is possible to establish this line of separation, it seems necessary to establish one or several parameters enabling to objectively realise the state of an analysed part. That is what is defined below by establishing the reference database.

Establishing the reference database first consists of taking a colorimetric measurement for each one of the first samples and by deducing the values L', a' and b' of the parameters L, a, b of the CIELAB colorimetric space, from at least one colorimetric measurement.

It must first be noted, that the values of the parameters L, a, b can be obtained from several colorimetric measurements in each zone where the measurement is taken, in other words, to establish the database or when it is wanted to test a determined zone of a part, as this will be explained later.

Figure 5:
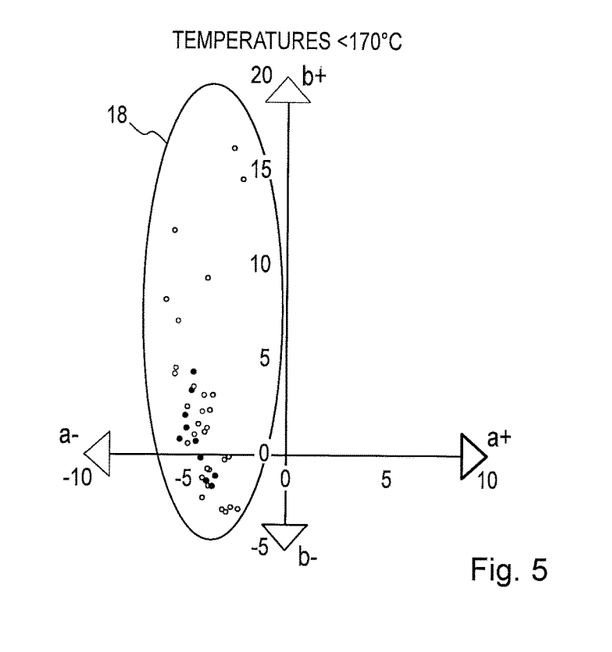
FIG. 5 is a schematic view of a graph where each point represents a sample from FIG. 3 having been subjected to a vitreous transition temperature of the tested material, each point being placed on the graph according to the values of the parameters a and b, thereof, a being represented on the x-axis and b being represented on the y-axis.
Figure 6:
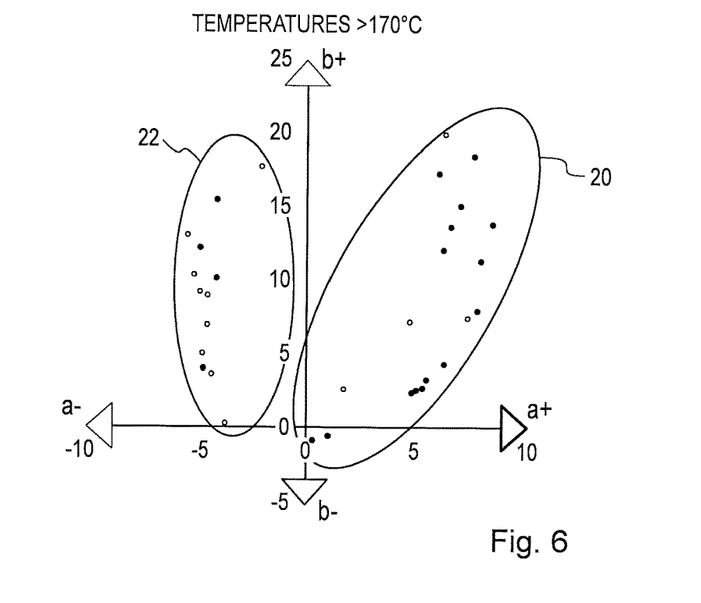
FIG. 6 is a schematic view of a graph where each point represents a sample from FIG. 3 having been subjected to a higher temperature than the vitreous transition temperature of the polymer material, each point being placed on the graph according to the values of the parameters a and b, thereof, a being represented on the x-axis and b being represented on the y-axis.

Now reference is made to FIGS. 5 and 6, each representing a graph where each point represents a first sample from FIG. 3, each point being placed on the graph according to the values of the parameters a and b thereof, a being represented on the x-axis and being represented on the y-axis. In FIG. 5, the first samples have been subjected to a temperature lower than the vitreous transition temperature of the polymer material, here 170° C., and in FIG. 6, the first samples have been subjected to a temperature higher than said vitreous transition temperature.

In FIG. 5, it has been observed that a group 18 of points is found at the values of the parameter having a value of less than zero whereas, in FIG. 6, for the first samples having been subjected to a temperature higher than 170° C., it has been observed that a group 20 of values of the parameter a are higher than zero. Consequently, it is possible to discriminate on the thermal state, in other words, the heating of a given zone of a part, from the measurement of this parameter. It will be noted that in FIG. 6, a second group 22 has values of the parameter a which are less than zero, but these points correspond to very low exposure times, less than 10 hours, which are not to be considered. On the graph in FIG. 5, it has also been observed that the variation is made mainly along the axis b, this variation enabling to highlight the yellowing by natural ageing over time of the polymer and of the resin in the case of a fan casing. This variation along the axis b is also visible in FIG. 6.

Thus, it is understood that it is possible, with a colorimetric measurement in the CIELAB space, to differentiate between the natural ageing of the fan case and an accidental overheating of by comparing with a reference database.

To each first sample 12, it is calculated that $\Delta a' = a' - a'_{ref}$, $\Delta b' = b' - b'_{ref}$ and $\Delta L' = L' - L'_{ref}$, where:

$a'_{ref}$, $b'_{ref}$ et $L'_{ref}$ respectively correspond to the values of the parameters a, b, L of the CIELAB colorimetric space, these values having been obtained on a second sample 14 made of a polymer material, in particular, of reinforcing fibres, having the same time of existence as said first sample considered, and having been kept at a temperature within a range of temperatures, such as that of preserving the mechanical integrity of the second sample 14, or such as a range between 0 and 40° C., which could further consider the exposure to rays in the ultraviolet field.

The colorimetric measurement on the second sample 14 associated with each measurement of a first sample 12 can be taken with the reference sample 14 that has been observed under the conditions stated in the previous paragraph.

For each first sample 12, a test is then carried out, aiming to determine the mechanical properties thereof, in order to determine the ability or not thereof to constitute a sample that can be used under the determined conditions. Thus, it is determined if the heating subjected by each first sample makes it useable or not. The test carried out can comprise at least one step for mechanically testing the part, for example, by traction and/or compression.

Finally, a comparison of the data from the tests with the values $\Delta a'$, $\Delta b'$ et $\Delta L'$ contained in the reference database is made, in order to establish the thresholds A1, A2, B1 and L1. The threshold A1 corresponds to a threshold beyond which it is considered that the fan case 10 must be arranged to be subjected to a more in-depth inspection of the zone to be tested (FIG. 7).

Figure 7:
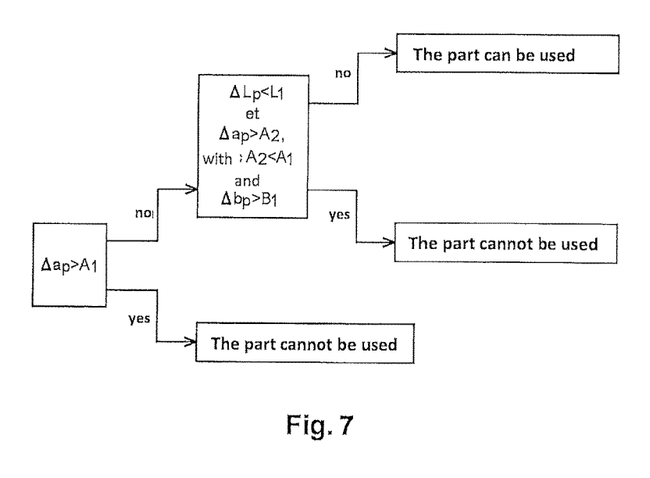
FIG. 7 is a flowchart of the functioning of the decision-making method during a step of non-destructive testing on a given zone to be tested, of a determined part such as the casing from FIG. 1.

To carry out a non-destructive test operation on the casing 10 from FIG. 1, first, the following steps are carried out, schematised in FIG. 7:

a) taking at least one colorimetric measurement on said determined zone 24 to be tested of the casing 10 and obtaining the value $a_p$ of the parameter a of the CIELAB colorimetric space, b) taking at least one colorimetric measurement on a reference zone 26 of the casing 10 and obtaining the value $a_{p/ref}$ of the parameter a of the CIELAB colorimetric space, c) calculating $\Delta a_p = a_p - a_{p/ref}$, d) establishing a risk of heating said determined zone to be tested if $\Delta a_p$ is higher than a threshold value A1.

The reference zone 26 of the casing 10 is a zone which has not suffered thermal damage.

In the case where the value $\Delta a_p$ is lower, a second step is carried out, aiming to determine if the part must undergo (or not) a test all the same, this time considering the value $b_p$ of the parameter b and the value $L_p$ of the parameter L obtained from the colorimetric measurement on the zone 24 to be tested of the casing, as well as the value $b_{p/ref}$ of the parameter b and the value $L_{p/ref}$ of the parameter L obtained from the colorimetric measurement on the reference zone 26 of the casing.

The method then consists of calculating $\Delta b_p = b_p - b_{p/ref}$ and calculating $\Delta L_p = L_p - L_{p/ref}$, and establishing a risk of heating said determined zone 24 to be tested if all the following conditions are checked:

$\Delta a_p$ is higher than a threshold value A2, A2 being lower than A1, $\Delta b_p$ is higher than a threshold value B1, $\Delta L_p$ is lower than a threshold value L1.

In this case, it is looked to determine if the tested zone 24 has a greater yellowing than the threshold value B1, if the clarity $\Delta L_p$ is low, in other words, lower than the threshold L1 while having a $\Delta a_p$ higher than a threshold value A2 lower than A1.

If one of the conditions above is not checked, the zone 24 to be tested is considered as not being damaged and the casing 10 can be used.

The non-destructive testing by colorimetry operation can be carried out under the wing of the aircraft, which enables to have a quick and reliable decision regarding the placing or not of the casing and reduces the unnecessary maintenance operations.

The parameters A1, A2, B1, L1 must be established to each type of part 10 and are therefore connected to the material of said part and also depend on the colorimetric measuring device.

Thus, in an example of taking colorimetric measurements with a Konica Minolta CM700d colorimeter, A1 is equal to 4.3, A2 is equal to −1, B1 is equal to 12.6 and L1 is equal to −0.9.

From the aforementioned colorimetric measurements contained in databases, it is possible to determine the time period during which the tested zone has been subjected to determined temperature, as well as this temperature.

For this, the colour difference $\Delta E_p = \sqrt{\Delta L_p^2 + \Delta a_p^2 + \Delta b_p^2}$ is calculated for the tested zone by using the colorimetric measurements obtained on the tested zone and on the reference zone of the analysed casing. For each one of the first samples, the colour difference $\Delta E' = \sqrt{\Delta L'^2 + \Delta a'^2 + \Delta b'^2}$ is also calculated from the values $\Delta L'$, $\Delta a'$ and $\Delta b'$. From the values $\Delta E'$, it is possible to trace the development of $\Delta E'$ over time for several determined temperatures as this is represented in FIGS. 8 and 9.

Figure 8:
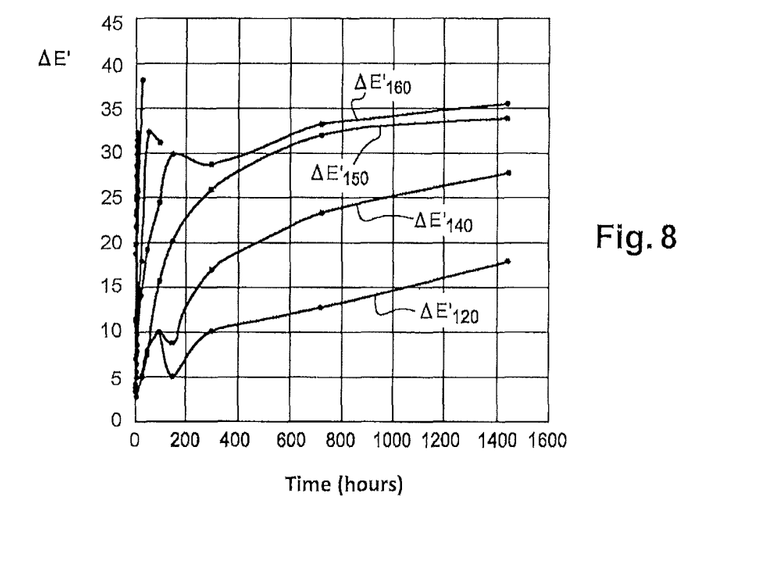
FIG. 8 is a graph representing the development in the colour difference over time for the samples from FIG. 3.

FIG. 8 represents the development of $\Delta E'$ over time for the temperatures 120, 140, 150 and 160° C., these curves are respectively referenced $\Delta' E_{120}$, $\Delta E'_{140}$, $\Delta E'_{150}$ and $\Delta E'_{160}$.

To avoid the colour difference development curves being impacted by the non-relevant values of $\Delta E'$ because of a very clear colouring or a colouring that is too dark, the points associated with such values $\Delta E'$ are removed. A very clear colouring can be due to an exposure to a low temperature for a relatively short time period. This zone corresponds to the zone 28 in FIG. 3 and cannot validly be considered in the colorimetric analysis. A too dark colouring can be due to an exposure to a too high temperature for a significant time period. This zone corresponds to the zone 30 in FIG. 3 and cannot validly be considered in the colorimetric analysis.

Figure 9:
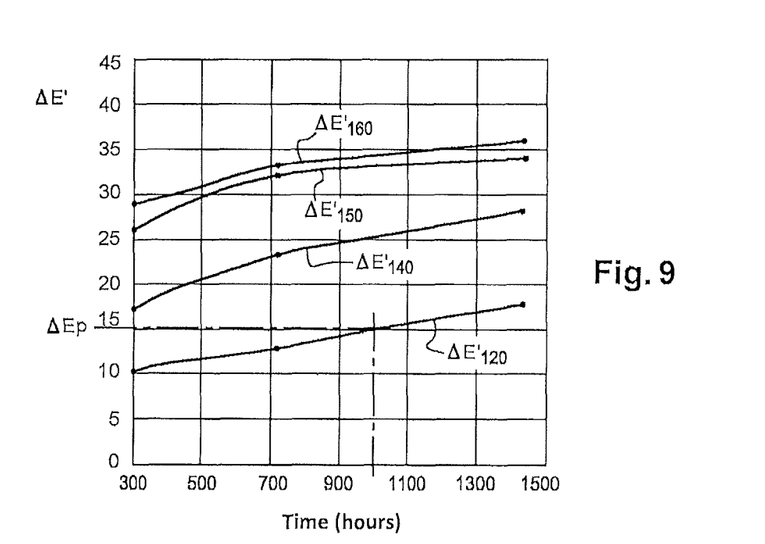
FIG. 9 is a larger-scale graph of a given zone of the graph from FIG. 8.

Therefore, the situation therefore is limited to the relatively long time of exposure, longer than 300 hours, as this is represented in FIG. 9. With this graph, it is possible from a measurement $\Delta E_p$ obtained on a given zone of a casing, to determine the temperature of exposure by tracing the constant ordinate line $\Delta E_p$ and searching for the intercepted curve which therefore indicates the temperature subjected to by said tested zone and the exposure temperature represented by the abscissa of the intersection point.

The invention claimed is:

1. A method for non-destructively testing a heating of a determined zone to be tested of a part made of a polymer material, the method comprising the following steps:
   a) taking at least one colorimetric measurement on said determined zone to be tested and obtaining values $a_p$, $b_p$ and $L_p$ of parameters a, b and L of a CIELAB colorimetric space,
   b) taking at least one colorimetric measurement on a reference zone of the part and obtaining values $a_{p/ref}$, $b_{p/ref}$ and $L_{p/ref}$ of the parameters a, b and L of the CIELAB colorimetric space,
   c) calculating a color difference $\Delta L'_p$ between the colorimetric measurements obtained in steps a) and b),
   d) from the value $\Delta E_p$ obtained in step c), determining a time period during which said determined zone to be tested of the part has been subjected to a determined heating temperature and determining said heating temperature by using a reference database comprising values $\Delta E'$ of color differences obtained from a plurality of samples made of a polymer material that has been subjected to a determined temperature for a determined time period.

2. The method according to claim 1, further comprising the following steps:
   tracing a graph of a development of $\Delta E'$ over time for several determined temperatures, and
   carrying out step d) by looking for an intersection of a constant ordinate line $\Delta E'_p$ with one of the graphs of the development of $\Delta E'$ over time.

3. The method according to claim 1, wherein establishing the reference database comprises, for each first sample, the following steps:
   obtaining values L', a', and b' of the respective parameters L, a, b, of the CIELAB colorimetric space, from at least one colorimetric measurement of said first sample,
   calculating $\Delta a' = a' - a'_{ref}$, calculating $\Delta b' = b' - b'_{ref}$ and calculating $\Delta L' = L' - L'_{ref}$ where:
      $a'_{ref}$, $b'_{ref}$ and $L'_{ref}$ correspond respectively to values of the parameters a, b, L of the CIELAB colorimetric space, these values having been obtained on a second sample made of reinforcing fibres, having a same time of existence as said first sample considered and having been kept at a temperature within a range of temperatures to preserve mechanical integrity of the second sample,
   calculating the color difference $\Delta E'$ between the first sample and the second sample.

4. The method according to claim 1, wherein each value considered of the parameters L, a, b of the CIELAB colorimetric space is obtained by taking an average of at least five successive colorimetric measurements at the determined zone to be tested.

5. The method according to claim 1, wherein the polymer material comprises reinforcing fibres.

6. The method according to claim 1, further comprising a step of cleaning a surface whereon a colorimetric measurement is intended to be taken.

7. The method according to claim 3, wherein the range of temperatures is a range between 0 and 40° C.

* * * * *

UNITED STATES PATENT AND TRADEMARK OFFICE
CERTIFICATE OF CORRECTION

PATENT NO. : 10,203,276 B2
APPLICATION NO. : 15/901509
DATED : February 12, 2019
INVENTOR(S) : Jean-Louis Romero et al.

It is certified that error appears in the above-identified patent and that said Letters Patent is hereby corrected as shown below:

In the Claims

In Column 8, Line 5, in Claim 1 delete "calculating a color difference $\Delta L'_p$ between the colorimetric measurements obtained in steps a) and b)," and insert -- calculating a color difference $\Delta E_p$ between the colorimetric measurements obtained in steps a) and b), --

Signed and Sealed this
Twentieth Day of August, 2019

Andrei Iancu
*Director of the United States Patent and Trademark Office*